United States Patent
Calleia

[19]

[11] Patent Number: 6,079,687
[45] Date of Patent: Jun. 27, 2000

[54] FOOT PEDAL CONTROL HOLDERS

[76] Inventor: Gregory C. Calleia, 464 Anthony St., Glen Ellyn, Ill. 60137

[21] Appl. No.: 09/138,176

[22] Filed: Aug. 21, 1998

[51] Int. Cl.[7] .................................................. F16M 3/00
[52] U.S. Cl. ...................................... 248/346.01; 248/694
[58] Field of Search ........................... 248/346.01, 346.11, 248/127, 51, 158, 694; 433/101; 211/126.4

[56] References Cited

U.S. PATENT DOCUMENTS

| | | | |
|---|---|---|---|
| 3,113,680 | 12/1963 | Frater et al. ......................... | 211/126.4 |
| 3,237,306 | 3/1966 | Staunt ................................... | 433/101 X |
| 4,041,609 | 8/1977 | Bresnahan et al. ..................... | 433/101 |
| 4,417,875 | 11/1983 | Matsui .................................... | 433/101 |
| 4,523,911 | 6/1985 | Braetsch et al. ........................ | 433/101 |

*Primary Examiner*—Ramon O. Ramirez
*Attorney, Agent, or Firm*—Banner & Witcoff, Ltd.

[57] ABSTRACT

A kit for stabilizing floor pedal controls of the type used by dentists and others to control dental and medical equipment and the like includes a molded plastic plate with a vertical wall for receiving and supporting a foot pedal control and connecting lugs along the sides of the plate for connecting adjacent plates and thus maintaining separate foot pedal controls in a fixed position relative to one another.

12 Claims, 2 Drawing Sheets

FIG.3
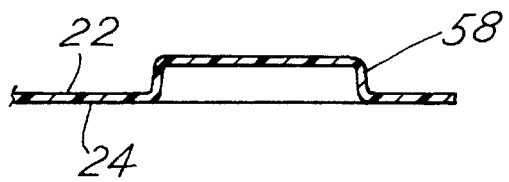
FIG.4 {
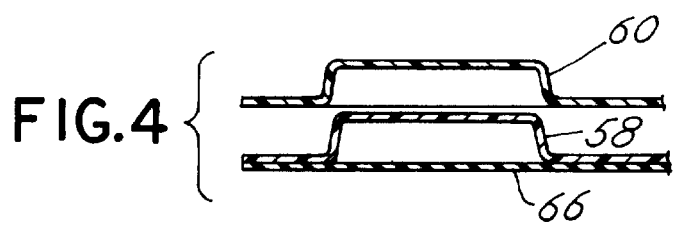
}
FIG.5
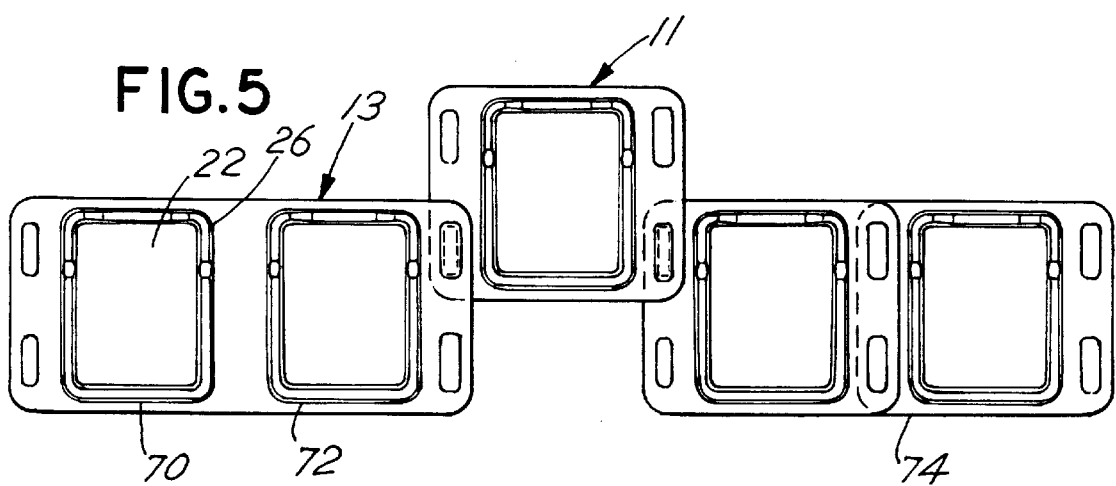

FOOT PEDAL CONTROL HOLDERS

BACKGROUND OF THE INVENTION

This invention relates to a foot pedal control retainer device or holder especially useful in combination with foot pedals that operate medical instruments.

Dentists, when performing various procedures, typically require their patient to be positioned in a dental chair which has the capability of being adjustable. That is, the chair back may be lowered or raised. The entire chair may be raised or lowered or turned. A leg support may also need to be raised or lowered.

Further, a dentist typically must operate various dental tools while adjusting the position of a chair or other patient support device. As a result, in order to simultaneously effect an appropriate number of movements or motions, foot pedal controls are often supplied for operating the dental chair, for example, or for operation of certain dental instruments. Foot controls, in combination with switches and controls that are manually operated, enable the dental physician or technician to easily and efficiently treat a patient. Physicians also rely upon instruments and patient support devices such as chairs or tables which may be operated by means of a foot pedal control. Others who use foot pedal controls include machinists and individuals involved in various manufacturing operations.

Mere placement of a number of pedal operated controls on the floor next to an operating station, however, is not necessarily a satisfactory means for properly positioning foot pedal controls. For example, the controls may slide on the floor or become tangled with one another or otherwise move relative to one another so as to encumber the operating ability and techniques of the physician, dentist or the like. Thus there has developed a need for providing a means to position and retain in a known position foot pedal controls.

SUMMARY OF THE INVENTION

Briefly, the present invention comprises a kit for stabilizing floor pedal controls of the type typically used by physicians, dentists and others. The kit includes at least two control pedal holders. The pedal holders each have a similar construction and are adapted to be connected one to the other to maintain separate foot pedal controls in a relative spaced relationship and stationary position one with respect to the other. Additionally, the foot pedal control holders are designed to adhere or frictionally engage a surface such as a floor surface. Further, the holders are designed to easily receive foot pedal controls of various size and configuration and to retain those foot pedal controls in a fixed orientation for use by a physician, dentist or other user. The holders may be color coded to facilitate identification by the user. They are connectable one to the other by engagement of lugs and recesses molded into each foot pedal holder.

Thus it is an object of the invention to provide an improved kit for stabilizing and positioning floor mounted foot pedal controls.

It is a further object of the invention to provide an economical mechanism for holding foot pedal controls in a desired position and for maintaining a series of foot pedal controls in a fixed relationship with respect to one another.

Another object of the invention is to provide an inexpensive foot pedal control holder construction fabricated from molded or formed plastic wherein the construction is comprised of a horizontal plate with a vertical support wall for receipt and retention of a foot pedal control.

Another object of the invention is to provide a foot pedal control holder construction wherein a single or unitary foot pedal control may be retained by the construction and further where means are provided for connecting separate foot pedal control holders.

These and other objects, advantages and features of the invention will be set forth in the detailed description which follows.

BRIEF DESCRIPTION OF THE DRAWING

In the detailed description which follows, reference will be made to the drawing comprised of the following figures:

FIG. 3 is a partial cross-sectional view of the holder of FIG. 2 taken along the line 3—3;

FIG. 4 is a partial cross-sectional view of the holder of FIG. 2 taken along the line 4—4; and FIG. 5 is a top plan view of a series of connected foot pedal control holders of the type which are the subject matter of the invention.

DESCRIPTION OF THE PREFERRED EMBODIMENT

Figure 1:
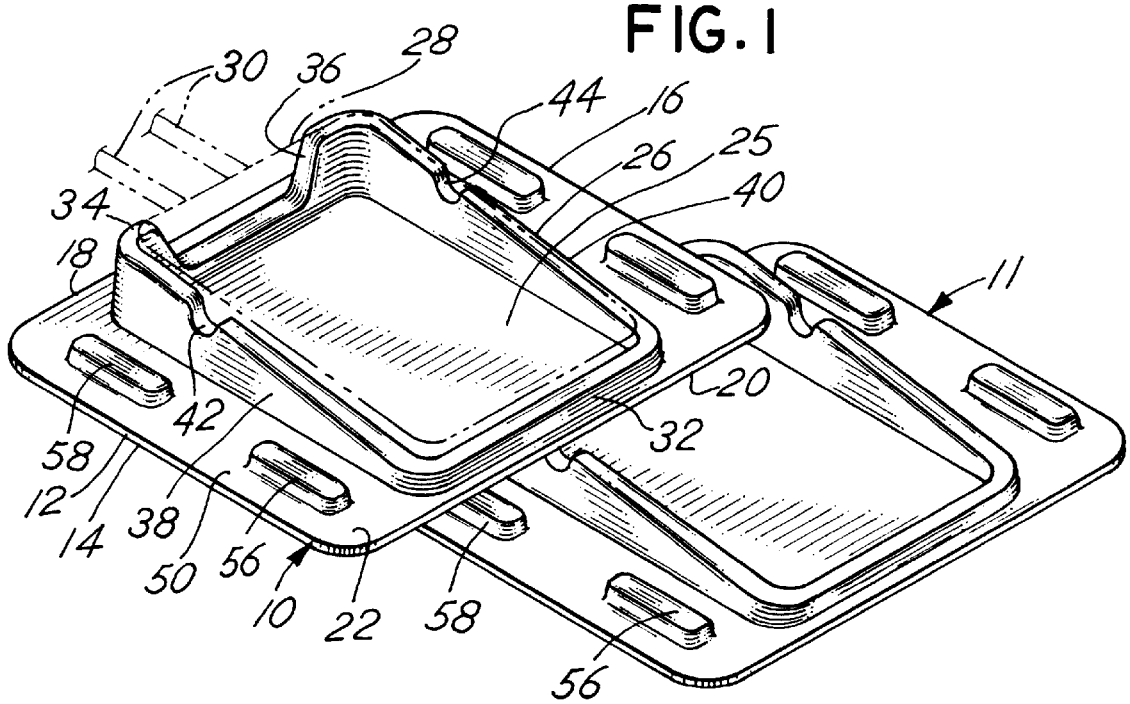
FIG. 1 is an isometric view of a pair of foot pedal control holders of the invention depicting the manner in which a foot pedal control may be retained thereby.
Figure 2:
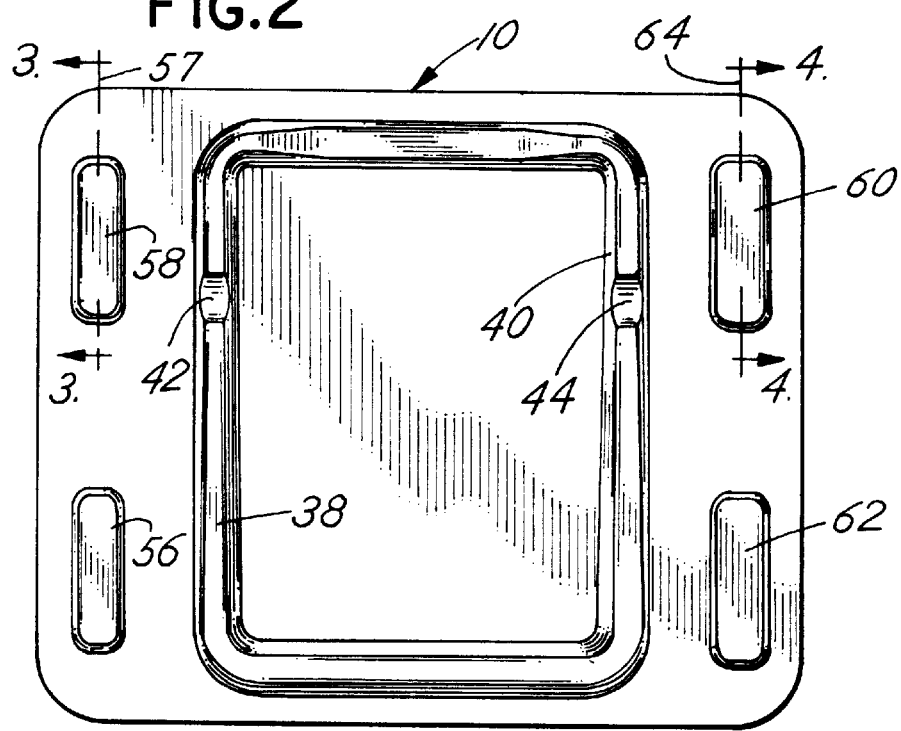
FIG. 2 is a top plan view of a holder of the type depicted in FIG. 1.

Referring to the figures, and in particular FIG. 1, a kit of foot pedal control holders includes two or more structures of the type depicted in FIG. 1. Thus with respect to the following description, like numbers relate to like parts for each of the separate units, elements or foot pedal control holders such as holders 10 and 11 in FIG. 1. The foot pedal control holder 10 includes a flat, planar plate 12 which is generally rectangular and includes opposite sides or edges 14 and 16, top side or edge 18 and a bottom side or edge 20. Further, the holder 10 includes a top surface 22 and a bottom surface 24. The foot pedal control holder 10 of the invention is typically made from a molded plastic material such as polyethylene sheet.

Integrally molded into or on the horizontal plate 12 is a vertical, circumferential, polygonal wall 26. The wall 26 in the embodiment shown is rectangular and conforms with the outside or periphery of a typical foot pedal control 28 such as shown in phantom in FIG. 1 having a lead or wire 30. The wall 26 includes a forward section 32 and a rear section 34 with a slot or groove 36 for receipt of the control lead 30. Tapered side walls 38 and 40 connect the higher elevation, vertical rear wall section 34 with the lower elevation, vertical forward wall section 32. In this manner, the foot pedal 28, which usually includes a pivotal, angled platform that may be pivoted to effect control, will fit within the wall 26. Thus the top surface 25 of the foot pedal control 28 will project above the wall 26 so that it may be easily operated by foot movement.

Additional grooves such as groove 42 and 44 may be included in the side walls 38 and 40 for receipt of projections, such as hinge pins, projecting from the side of the foot pedal control 28. In the embodiment depicted the wall 26 has a rectangular plan view configuration and the vertical sides 38 and 40 are generally parallel to the sides 14 and 16, respectively, of plate 12. Plate 12 is also typically rectangular. The four sides or edges of the rectangle forming the plate 12 are generally parallel respectively to the four sides or sections forming the wall 26. This is not a limiting feature of the invention, however.

On opposite sides of the side walls 38 and 40 are lands 50 and 52. The lands 50 and 52 thus separate the edges 14 and 16 of plate 12 from the wall 26, i.e., side walls 38, 40. Formed on the land 50 are first and second vertically projecting lugs 56 and 58. In the embodiment depicted, the lugs 56 and 58 are elongated and project vertically above the top surface 22 of the plate 12. The lugs 56 and 58 define a longitudinal axis 57 which is generally parallel to the wall 38.

On the opposite side of the wall 40 between the wall 40 and the edge 16 on the land 52 is a detent or recess 60 and a second recess 62. The recesses 60 and 62 also are elongated and lie along a longitudinal axis 64 parallel to axis 57 of lugs 56 and 58. Thus axis 57 and axis 64 are generally parallel in the embodiment shown. Additionally, the recesses 60, 62 defined in the plate 12 are configured and have an internal dimension which enables them to frictionally receive lugs 56, 58 of the next adjacent holder 12. This is depicted in FIG. 4. In this manner, the separate holders 10 and 11 may be engaged with one another.

The bottom surface 24 of the plate 12 is at least partially coated or covered with a frictional material such as a rubber mat 66 to facilitate maintaining the plate 12 in a desired position on the floor. The plate 12 is flexible to enable the plate 12 to remain positioned on the floor even though multiple plates 10, 12 are attached one to the other.

In the embodiment shown, the lugs 56, 58 and the recesses 60, 62 are elongated or elliptical in shape. Various other configurations, however, maybe used including hexagonal, round, square, rectangular or the like. The axes 57 and 64 in the embodiment shown are also parallel to the sides 38 and 40 of wall 26. Other orientations may be utilized.

Additionally the holders may be offset with respect to one another, for example, as shown in FIG. 5. There a holder 11 is offset with respect to another holder 13 inasmuch as one lug 56 is received into the recess or detent 60. Also as shown in FIG. 5, the holders may be linked one to the other side-by-side or offset in opposite directions. Multiple holders may be connected to form a kit having more than two holders. A single holder may include first and second integrally molded foot pedal retaining walls such as the walls 70 and 72 associated with the foot pedal holder 13.

Interior surface or top surface 22 within wall 26 may include fastening material such as a Velcro material or releasable adhesive material to facilitate holding a foot pedal control in position. Plates, such as plate 12, may be pie-shaped or trapezoidally shaped. Holders which do not include any foot pedal wall may be used as a connector 74 between plates. The holders may be color coded so that a quick glance will enable the physician, dentist or other person to determine a correlation between the foot pedal and an operation to be effected thereby.

Thus, there are many variations and alternative features which may be incorporated with the subject matter of the invention. The invention is, therefore, to be limited only by the following claims and their equivalents.

What is claimed is:

1. A kit for stabilizing floor pedal controls of the type used by physicians, dentists and others for control of instruments and devices comprising, in combination:

at least a first and a second, generally planar floor mounted pedal holder;

each of said holders comprised of a molded plastic plate including a bottom surface, a top surface, a generally polygonal configuration, and a molded polygonal, vertical wall projecting from the top surface to form a retaining enclosure for a foot pedal control;

said first floor holder further including at least two projecting lugs from the top surface adjacent one side of the plate intermediate said side and the molded polygonal wall;

said second floor holder further including at least two lug receiving detents in the bottom surface adjacent one side of said second holder plate; and said detents having the same pattern as the lugs to thereby receive the lugs and releasably retain the holders joined together.

2. The kit of claim 1 wherein the plates are rectangular and the walls are rectangular with the sides of the plates and walls parallel, and wherein the detents are intermediate a side of the second plate and a wall on said plate.

3. The kit of claim 1 wherein the first holder includes only two spaced lugs and the second holder includes two spaced detents, said detents congruent with the lugs, said lugs each having a substantially identical configuration and cooperative with a detent.

4. The kit of claim 1 wherein the plates are rectangular and each plate includes a pair of lugs positioned on one side of the plate and a pair of detents on the opposite side of the plate.

5. The kit of claim 1 wherein the walls of each plate are rectangular and include at least one groove therethrough for passage of a control line to a foot pedal control retained by the wall.

6. The kit of claim 1 wherein the walls are inclined to accommodate a foot pedal control.

7. The kit of claim 1 wherein the bottom surface includes means for frictionally engaging a floor surface.

8. A foot pedal holder comprising, in combination:

a generally polygonal, molded, horizontal plastic plate with side edges and having a top surface with a molded, vertical plastic wall on the top surface and a bottom surface, said vertical wall having at least two opposite sides spaced from the edges of the plate, to define a first land and a second land, said first land including at least two spaced lugs projecting from the top surface and said second land including at least two spaced detents in the bottom surface have a pattern substantially the same as the pattern defined by the lugs whereby the detents of the holder may receive the lugs of an adjacent holder.

9. The holder of claim 8, wherein the detents and lugs are elongate and generally parallel to a side, and wherein the detents are compatible with both lugs whereby the lugs may engage all the detents to thereby align adjacent holders or less than all the detents to thereby offset adjacent connected holders.

10. The holder of claim 8 wherein the wall is rectangular and includes at least one groove for receipt of a control line to a pedal control retained by the wall.

11. The holder of claim 8 wherein the wall has sides parallel to the sides of the plate and the plate is rectangular.

12. The holder of claim 8 wherein the wall has a rectangular configuration including one pair of inclined opposite side walls configured for access and control of an inclined foot pedal retained by the wall.

* * * * *